US 8,313,530 B2

(12) United States Patent
Bhatnagar et al.

(10) Patent No.: US 8,313,530 B2
(45) Date of Patent: Nov. 20, 2012

(54) TOTAL KNEE ARTHROPLASTY SYSTEM

(75) Inventors: Mohit K. Bhatnagar, Potomac, MD (US); Jack Y. Yeh, North Potomac, MD (US)

(73) Assignee: JMEA Corporation, Rockville, MD (US)

( * ) Notice: Subject to any disclaimer, the term of this patent is extended or adjusted under 35 U.S.C. 154(b) by 1114 days.

(21) Appl. No.: 11/673,991

(22) Filed: Feb. 12, 2007

(65) Prior Publication Data

US 2008/0195108 A1    Aug. 14, 2008

(51) Int. Cl.
*A61F 5/00*    (2006.01)
*A61F 2/38*    (2006.01)

(52) U.S. Cl. ........................ 623/20.14; 606/87
(58) Field of Classification Search ............... 606/79–85, 606/86 R, 87–89; 623/20.14–20.36
See application file for complete search history.

(56) References Cited

U.S. PATENT DOCUMENTS

| | | | |
|---|---|---|---|
| 4,344,192 A | 8/1982 | Imbert | |
| 4,502,483 A | 3/1985 | Lacey | |
| 4,722,330 A | 2/1988 | Russell et al. | |
| 4,825,857 A | 5/1989 | Kenna | |
| 4,944,760 A * | 7/1990 | Kenna | 128/898 |
| 5,454,816 A | 10/1995 | Ashby | |
| 5,593,450 A | 1/1997 | Scott et al. | |
| 5,776,201 A * | 7/1998 | Colleran et al. | 623/20.15 |
| 6,258,095 B1 | 7/2001 | Lombardo et al. | |
| 6,494,914 B2 * | 12/2002 | Brown et al. | 623/20.3 |
| 6,500,179 B1 * | 12/2002 | Masini | 606/88 |
| 6,558,391 B2 | 5/2003 | Axelson, Jr. et al. | |
| 6,589,283 B1 * | 7/2003 | Metzger et al. | 623/20.35 |
| 6,685,711 B2 | 2/2004 | Axelson, Jr. et al. | |
| 6,866,683 B2 | 3/2005 | Gerbec et al. | |
| 7,104,997 B2 * | 9/2006 | Lionberger et al. | 606/88 |
| 7,264,635 B2 * | 9/2007 | Suguro et al. | 623/20.14 |
| 7,527,650 B2 * | 5/2009 | Johnson et al. | 623/20.14 |
| 7,621,919 B2 * | 11/2009 | Williams et al. | 606/87 |
| 2003/0225458 A1 * | 12/2003 | Donkers et al. | 623/20.15 |
| 2004/0204760 A1 * | 10/2004 | Fitz et al. | 623/14.12 |
| 2005/0209701 A1 * | 9/2005 | Suguro et al. | 623/20.27 |
| 2006/0241635 A1 * | 10/2006 | Stumpo et al. | 606/87 |

OTHER PUBLICATIONS

Name: "unknown" "3D Knee Brochure" Date: "unknown".
Robinson, Raymond P., MD, "The Early Innovators of Today's Resurfacing Condylar Knees," The Journal of Arthroplasty, vol. 20, No. 1., Suppl. 1 2005.
International Search Report and Written Opinion, mailed Aug. 15, 2008, from PCT Application No. PCT/US08/53327.
International Preliminary Report on Patentability from related PCT Application No. PCT/US2008/053327 mailed Aug. 27, 2009.

* cited by examiner

*Primary Examiner* — Kevin T Truong
*Assistant Examiner* — Christopher Beccia
(74) *Attorney, Agent, or Firm* — Plumsea Law Group, LLC

(57) ABSTRACT

A total knee arthroplasty (TKA) set that includes a universal cutting jig for shaping the distal femur is disclosed. The universal cutting jig may be used to create a shaped femur that can be receive multiple and different TKA implant designs. A universal high flexion knee system adapted for left-right use is also disclosed.

28 Claims, 6 Drawing Sheets

TOTAL KNEE ARTHROPLASTY SYSTEM

BACKGROUND OF THE INVENTION

1. Field of the Invention

This invention relates to a total knee arthroplasty (TKA) system, in particular a TKA system that includes a universal cutting jig for shaping the distal femur and a multitude of TKA prosthesis designs that fit into the same shaped distal femur.

2. Description of Related Art

The TKA systems typically have a distinct profile to the distal femur integrating a surface specific to the system. This profile can be the same for the different sizes in a system, but typically is not the same for different articulating surface designs. Attempts to create cutting jigs and methods for shaping the distal femur are previously described. Lacey (U.S. Pat. No. 4,502,483) discloses a method for resecting and shaping the distal femur through the use of a cutting jig is a standard practice for preparing the femur. The method described by Lacey (U.S. Pat. No. 4,502,483) is incorporated by reference in its entirety. Russell et al. (U.S. Pat. No. 4,722,330) and Axelson et al. (U.S. Pat. No. 6,558,391) disclose a similar method for resecting and shaping the distal femur with various cutting jig designs specifically for receiving a knee prosthesis. Russell et al. (U.S. Pat. No. 4,722,330) and Axelson et al. (U.S. Pat. No. 6,558,391) are incorporated by reference in their entirety. The cutting jigs described in the aforementioned prior art addresses the need to shape the femur and the shaped profile is specific to a single TKA system design. The system specific profile requires that a specific set of instrumentation, including a cutting jig for shaping the distal femur, be provided. The specificity of the instruments to a TKA system limits the usage of the instrument set solely to one TKA design.

The methods and systems described by Lacey, Russel, and Axelson do not address the need for multiple TKA femoral component designs for a given shaped profile. The specificity of the cutting jig to a specific TKA system design requires multiple sets of instruments if more than one TKA system design is used by a particular surgeon. It is common for a surgeon to use several designs, as patients anatomies, pathologies, and lifestyles may dictate the need for a wide range of motions that no single TKA system design can provide.

Gerbec et al. (U.S. Pat. No. 6,866,683) discloses a modular TKA system that offers multiple designs with respect to the portion of the implant that integrates with the patients' bone. However, the design describes only one articulating shape profile, and the modular nature of the system is to allow for use of this system for primary or revision TKA. This system does not allow for flexibility with articulating surface profile. Furthermore, complex modular systems may be less desirable due to their inherent complexity and the increased number of regions or components that can each increase the risk for implant failure.

A general overview of the history of TKA systems can be found in Robinson, "The Early Innovators of Today's Resurfacing Condylar Knees," *The Journal of Arthroplasty*, Volume 20, Number 1 Supplement 1 2005, pages 2-26.

There is a need in the art for a TKA system that utilizes a universal cutting jig for a variety of TKA articulating profile designs. A system that solves this need will reduce the amount of instrumentation required for multiple TKA designs and will provide surgeons with more choices of TKA profiles for a given surgery.

SUMMARY OF THE INVENTION

A total knee arthoplasty system is disclosed. In one aspect, the invention provides a system for performing a total knee replacement surgery comprising: a jig configured to guide a cutting member in cutting a distal portion of a femur and resulting in a prepared distal surface, the prepared distal surface having a prepared shape; a first femoral component having a first proximal side; a second femoral component having a second proximal side; the first proximal side and the second proximal side being substantially similar and configured to engage the prepared shape; the first femoral component having a first distal side; the second femoral component having a second distal side; and wherein the first distal side is shaped differently than the second distal side.

In another aspect, the first femoral component includes a corresponding first tibial component.

In another aspect, the second femoral component includes a corresponding second tibial component.

In another aspect, a third femoral component includes a third proximal side being substantially similar to the first proximal side and wherein the third femoral component includes a third distal side that is shaped differently than either the first distal side or the second distal side.

In another aspect, the jig is smaller than a second jig, the second jig configured to guide the cutting member in cutting a second distal portion of a femur and resulting in a second prepared distal surface, the second prepared distal surface having a second prepared shape; wherein the second prepared shape is larger than the prepared shape.

In another aspect, the invention provides a method for performing a total knee replacement procedure comprising the steps of: preparing a distal femur by cutting the distal femur with a cutting device that is guided by a jig, and eventually forming a prepared distal femur with a first distal surface; selecting a selected knee prosthesis from a group of candidate knee prostheses, wherein the group of candidate knee prostheses includes candidate femoral components having similar proximal sides and having substantially different distal sides; wherein the proximal sides are configured to engage the first distal surface of the prepared distal femur; and associating the selected femoral component with the prepared distal femur.

In another aspect, the proximal sides of the candidate knee prosthesis femoral components include similar proximal surfaces configured to engage the prepared distal surface.

In another aspect, the group of candidate knee prostheses is associated with a first size.

In another aspect, the first group of candidate knee prostheses is associated with a second group of candidate knee prostheses.

In another aspect, the second group of candidate knee prostheses includes candidate femoral components having similar proximal sides and having substantially different distal sides.

In another aspect, the second group of candidate knee prostheses is associated with a second size.

In another aspect, the first size is different from the second size.

In another aspect, the invention provides a kit of parts comprising: a set of knee prostheses including a femoral component and a tibial component; each femoral component of the set of knee prostheses including a proximal side and a distal side; wherein the proximal side of each femoral component is substantially similar in size and shape; wherein the distal side of each femoral component is shaped differently;

and wherein each femoral component has a corresponding tibial component to match the distal side of the femoral component.

In another aspect, the kit of parts further comprises a cutting jig.

In another aspect, the set of knee prostheses are similar in size.

In another aspect, each femoral component is configured to be attached to a right femur or a left femur.

In another aspect, each knee prosthesis of the set of knee prostheses is capable of undergoing a high flexion angle.

In another aspect, the high flexion angle is about 150 degrees.

In another aspect, the jig is used to shape the distal end of a femur for attaching a femoral component.

In another aspect, the invention provides a system for performing a total knee replacement surgery on a left or right knee comprising: a jig configured to guide a cutting member in cutting a distal portion of a left femur and resulting in a prepared left distal surface, the prepared left distal surface having a first prepared shape; the jig configured to guide a cutting member in cutting a distal portion of a right femur and resulting in a prepared right distal surface, the prepared right distal surface having a second prepared shape; and wherein the first prepared shape and the second prepared shape are substantially identical and configured to receive a universal femoral component for use in either a right knee or a left knee.

In another aspect, the universal femoral component is an average of a left femoral component and a right femoral component.

In another aspect, the system includes a set of at least two universal femoral components.

In another aspect, the proximal sides of each universal femoral component in the set of universal femoral components are similar.

In another aspect, the distal sides of each universal femoral component in the set of universal femoral components are substantially different.

In another aspect, each universal femoral component of the set of universal femoral components is associated with a distinct tibial component.

In another aspect, the sizes of the universal femoral components are similar.

In another aspect, the invention provides a system for performing a total knee replacement surgery comprising: a jig configured to guide a cutting member in cutting a distal portion of a femur and resulting in a prepared distal surface, the prepared distal surface having a prepared shape; a first femoral component having a first proximal side; a second femoral component having a second proximal side; the first proximal side and the second proximal side being substantially similar and configured to engage the prepared shape; the first femoral component having a first distal side that is different from a second distal side of the second femoral component; and wherein each femoral component is configured to be used in a high flexion knee prosthesis. Generally, a high flexion knee is any knee that can bend beyond about 120 degrees.

In another aspect, the high flexion knee prosthesis is able to achieve a flexion angle in the range of 90-150 degrees.

In another aspect, the high flexion knee prosthesis is able to achieve a flexion angle in the range of 109-150 degrees.

In another aspect, the high flexion knee prosthesis is able to achieve a flexion angle in the range of 130-150 degrees.

In another aspect, the first femoral component is a universal femoral component that may be used with either a left femur or a right femur.

In another aspect, the prepared shape is configured to receive the universal femoral component.

In another aspect, the first distal end of the first femoral component is associated with a first tibial component.

In another aspect, the second distal end of the second femoral component is associated with a second tibial component.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
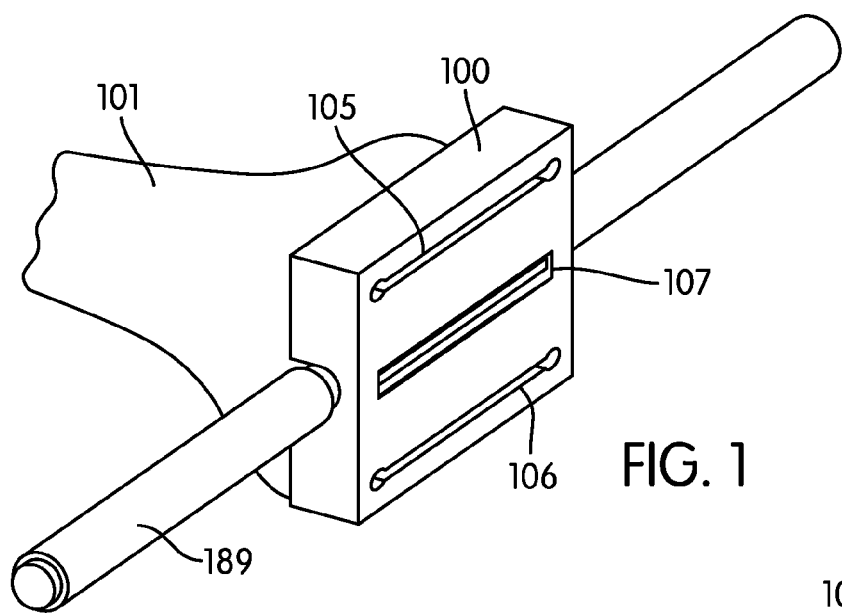
FIG. 1 is an isometric view of a preferred embodiment of a universal cutting jig mounted on a distal femur.
Figure 2:
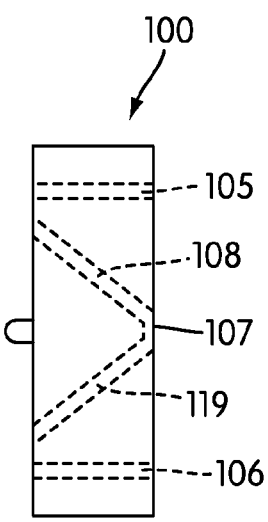
FIG. 2 is a schematic cross sectional side view of a preferred embodiment of a universal cutting jig.

FIGS. 1 and 2 show a preferred embodiment of a universal cutting jig 100 for shaping distal femur 101. Universal cutting jig 100 may be any device configured to shape the distal end of a femur. In some embodiments, universal cutting jig 100 may be rectangular, as seen in the current embodiment, however in other embodiments, universal cutting jig 100 may be configured to have any shape.

Generally, universal cutting jig 100 may be made of any material that is commonly used for making jigs. In some embodiments, universal cutting jig 100 may be made of metal or similar materials. In a preferred embodiment, universal cutting jig 100 may be made of a material including stainless steel. In some embodiments, stainless steel is used, however, titanium or any other suitable material may also be used.

Preferably, universal cutting jig 100 includes provisions for being temporarily fixed to distal femur 101. In some embodiments, universal cutting jig 100 may be attached to distal femur 101 using handle 189 or a similar device. In other embodiments, any type of clamp or other device may be used that are well known in the art for securing cutting jigs to femurs.

Universal cutting jig 100 may include provisions for shaping distal femur 101. In a preferred embodiment, the shaping of distal femur 101 is performed with the use of an oscillating surgical saw having a blade for cutting bone. The blade may be guided along defined cutting planes through distal femur 101 that are established with the use of the universal cutting jig 100.

In this preferred embodiment, universal cutting jig 100 may include first horizontal slot 105 and second horizontal slot 106. Preferably, universal cutting jig 100 may also include horizontal recess 107 that may be generally wider than horizontal slots 105 and 106. Additionally, universal cutting jig 100 may include first diagonal slot 108 and second diagonal slot 119. Diagonal slots 108 and 119 preferably extend through universal cutting jig 100. Each of these slots 105, 106, 108 and 119, as well as horizontal recess 107, are preferably configured to accept the cutting blade along predetermined cutting planes defined by slots 105, 106, 108 and 119. Thus, a surgeon may shape distal femur 101 in a precise manner, reducing the chances for unwanted deviations from the preferred shape for distal femur 101.

Figure 3:
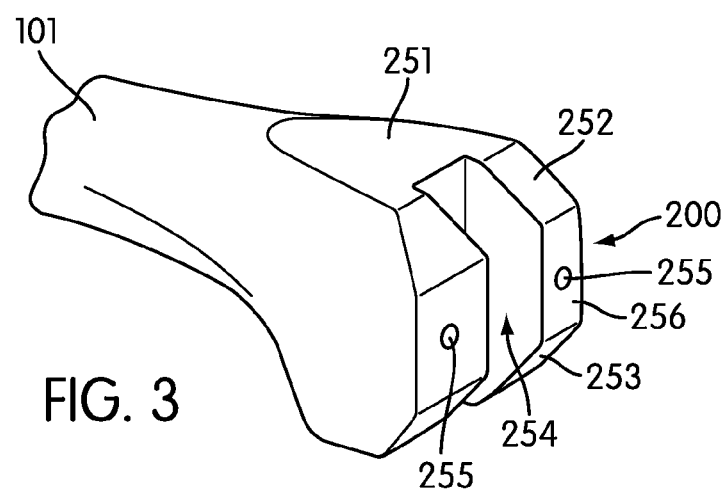
FIG. 3 is an isometric view of a preferred embodiment of a distal femur that has been shaped using the universal cutting jig.

FIG. 3 shows a preferred embodiment of the distal femur 101 after prepared distal surface 200 has been shaped with universal cutting jig 100. Generally, prepared distal surface 200 comprises individual planes that are formed using a cutting device in conjunction with universal cutting jig 100. First upper plane 251 is preferably associated with first horizontal slot 105. Likewise, first lower plane (not shown in FIG. 3) may be associated with second horizontal slot 106. Additionally, diagonal slots 108 and 119, as well as the associated diagonal slots on the second side of universal cutting jig 100, are preferably associated with first sloped surface 252 and second sloped surface 253. Holes 255 may have been formed to assist in attaching universal cutting jig 100 to distal femur 101. Finally, inner surfaces 254 and vertical surfaces 256 are generally prepared with a different type of tool or jig.

Figure 4:
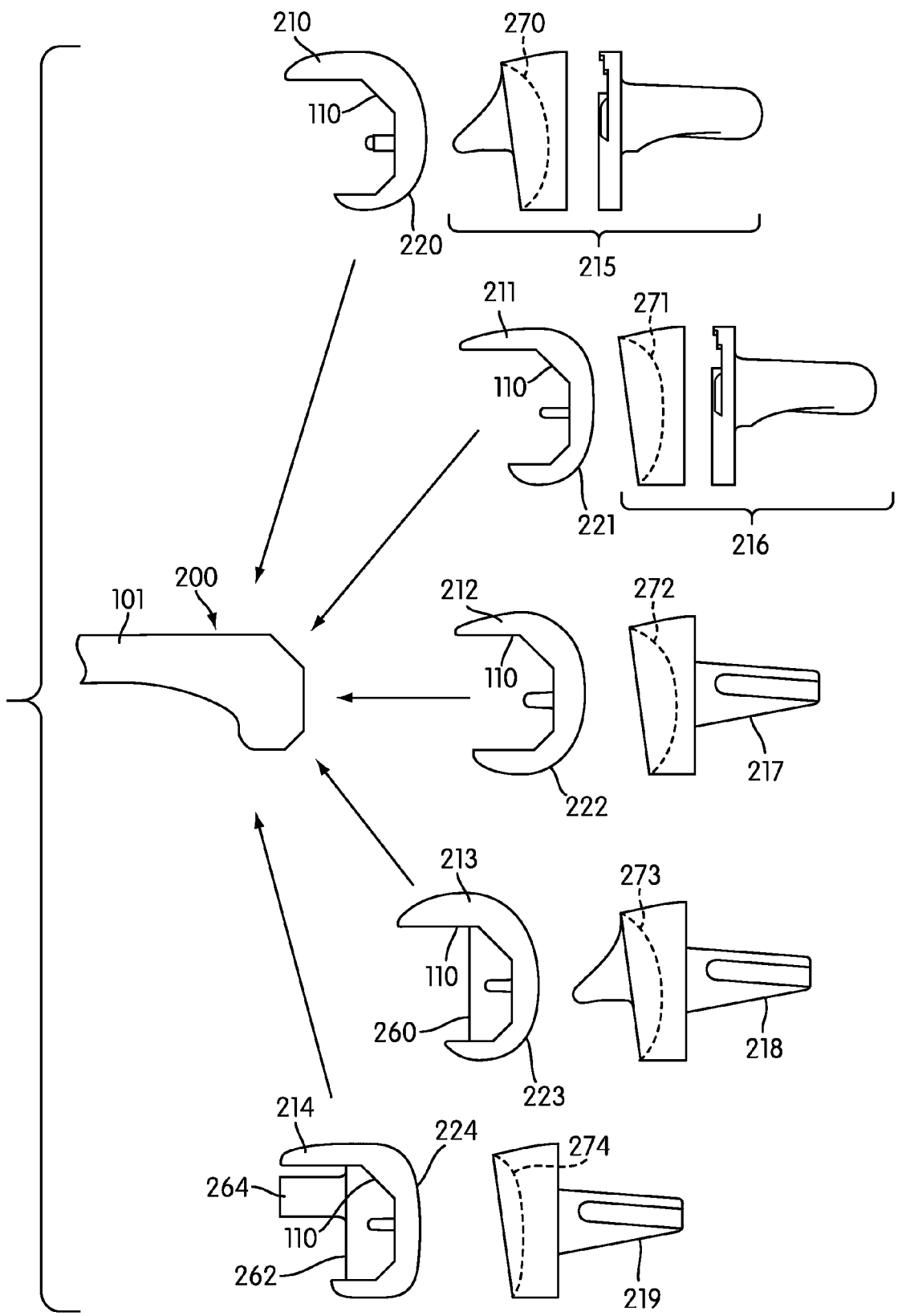
FIG. 4 is a side view of a preferred embodiment of five different TKA system designs having the same proximal surface for integrating with the shaped distal femur illustrated in FIG. 3 and different distal articulating surfaces.

Preferably, multiple knee prostheses may be associated with distal femur 101 as it has been shaped using universal cutting jig 100. FIG. 4 is a preferred embodiment of a set of candidate femoral and tibial components that may be associated with distal femur 101. Femoral and tibial components are pieces of a knee prosthesis configured to attach to the femur and tibia, respectively. Generally, a femoral component and a tibial component together make up a total knee arthoplasty (TKA) system.

In the current embodiment, distal femur 101 may be associated distinct femoral components from five different TKA systems. In this embodiment, distal femur 101 may be associated with first femoral component 210, second femoral component 211, third femoral component 212, fourth femoral component 213 and fifth femoral component 214. In this embodiment, first femoral component 210 is preferably configured with proximal side 110 that is shaped to fit together with distal surface 200 of distal femur 101. Likewise, each of the remaining femoral components 211-214 are preferably configured with a similar proximal side 110 that is shaped to fit together with distal surface 200 of distal femur 101. Proximal side 110 may include an optional projection or pin that mates with residual holes 255 (see FIG. 3) in distal femur 101. In other words, the preferred shape of prepared distal surface 200 is a specific geometry that, for a given size of implant, will mate with all five distinct femoral components.

Since each of the femoral components 210-214 have substantially similar proximal sides 110 for integrating with the shaped distal femur 101, this means a single universal cutting jig 100 may be used to prepare distal femur 101 for any number of compatible femoral components. As long as the femoral component includes a compatible proximal side 110, that femoral component may be used with the distal surface 200 that has been shaped using universal cutting jig 100. Although five distinct femoral components 210-214 are shown in this embodiment, other embodiments may include more or less than five distinct femoral components. Preferably, any additional femoral component that may be associated with distal femur 101 includes a proximal side substantially similar in shape to proximal side 110, in order to fit properly with distal surface 200.

In some embodiments, other facets may be included as part of the proximal side of a femoral component. For example, fourth femoral component 213, in the preferred embodiment, includes first side wall 260. Likewise, fifth femoral component 214 preferably includes second side wall 262 and protruding portion 264. These additional facets of proximal sides 110 of femoral components 213 and 214 may correspond to various additional surfaces of prepared distal surface 200 of distal femur 101 that may be configured using additional tools.

Each femoral component 210-214 also includes a distal side, configured to attach to various tibial components. As shown in FIG. 4, first femoral component 210 includes first distal side 220, second femoral component 211 includes second distal side 221, third femoral component 212 includes third distal side 222, fourth femoral component 213 includes fourth distal side 223, and fifth femoral component 214 includes fifth distal side 224.

Preferably, distal sides 220-224 may be different from one another in shape and design. As seen in FIG. 4, each distal surface 220-224 has a slightly different curvature. Distal sides 220-224 may have similar profiles to the distal sides of femoral components already offered by manufacturers of TKA systems. For example, first distal side 220 may be the profile of a TKA femoral component offered by Stryker Orthopedics while second distal side 221 may be similar to a profile offered by Zimmer Orthopedics. The remaining distal surfaces may be similar to other commercially available TKA systems or be unique or proprietary designs.

Each distal side 220-224 is preferably configured to mate with a distinct tibial component. A tibial component may be configured to attach to the tibia bone at one end, and to attach to or be associated with femoral component at another end. The connection between a femoral component and a tibial component then functions as the knee joint. In the example shown in FIG. 4, first femoral component 210 includes a corresponding first tibial component 215, second femoral component 211 includes a corresponding second tibial component 216, third femoral component 212 includes a corresponding third tibial component 217, fourth femoral component 213 includes a corresponding fourth tibial component 218, and fifth femoral component 214 includes a corresponding fifth tibial component 219.

Tibial components 215-219 preferably have inner surfaces to match with the femoral component designs. For example, first distal side 220 of first femoral component 210 is preferably shaped to fit within first inner surface 270 of first tibial component 215. The curved nature of first distal side 220 and first inner surface 270 preferably allows first femoral component 210 to slide against first tibial component 215. This configuration allows the TKA system to simulate the bending of a knee, as will be discussed in further detail below.

In a manner similar to first distal side 220 and first inner surface 270, second distal side 221 preferably fits within second inner surface 271 of second tibial component 216; third distal side 222 preferably fits within third inner surface 272 of third tibial component 217; fourth distal side 223 preferably fits within fourth inner surface 273 of fourth tibial component 218; and fifth distal side 224 preferably fits within fifth inner surface 274 of fifth tibial component 219. Each of these femoral components is preferably configured to slide within or with respect to the corresponding tibial components, in a manner similar to the movement described for first femoral component 210 and first tibial component 215.

Although FIG. 4 shows an embodiment with five possible femoral and tibial components, some embodiments may provide more or less than five possible femoral and tibial components. Any desired number of femoral and tibial components may be provided and it should be kept in mind that the embodiment shown in FIG. 4 is merely an example.

Providing similar proximal surfaces 110 to each femoral component 210-214 provides the surgeon with some flexibility in making decisions. In one example, a surgeon may decide which femoral component or TKA system to attach to distal femur 101 during a surgical procedure, even after distal femur 101 has been shaped, since each femoral component is configured to fit with a single preconfigured distal surface of distal femur 101. This decision making flexibility would not be possible with other TKA systems where a particular cutting jig is needed for each different TKA system. With these other TKA systems, once the distal femur has been shaped, only the corresponding femoral component may be implanted. For example, if the system offered by Stryker was used to shape the distal femur and it was later discovered during the surgery, and after the distal femur was shaped, that the system offered by Zimmer would be a more suitable design, the surgeon could not implant the Zimmer femoral component onto a distal femur shaped by the Stryker system.

Throughout the remainder of this detailed specification, any set of knee prostheses configured to attach to the same distal surface shape will be referred to as a universal TKA system.

Figure 5:
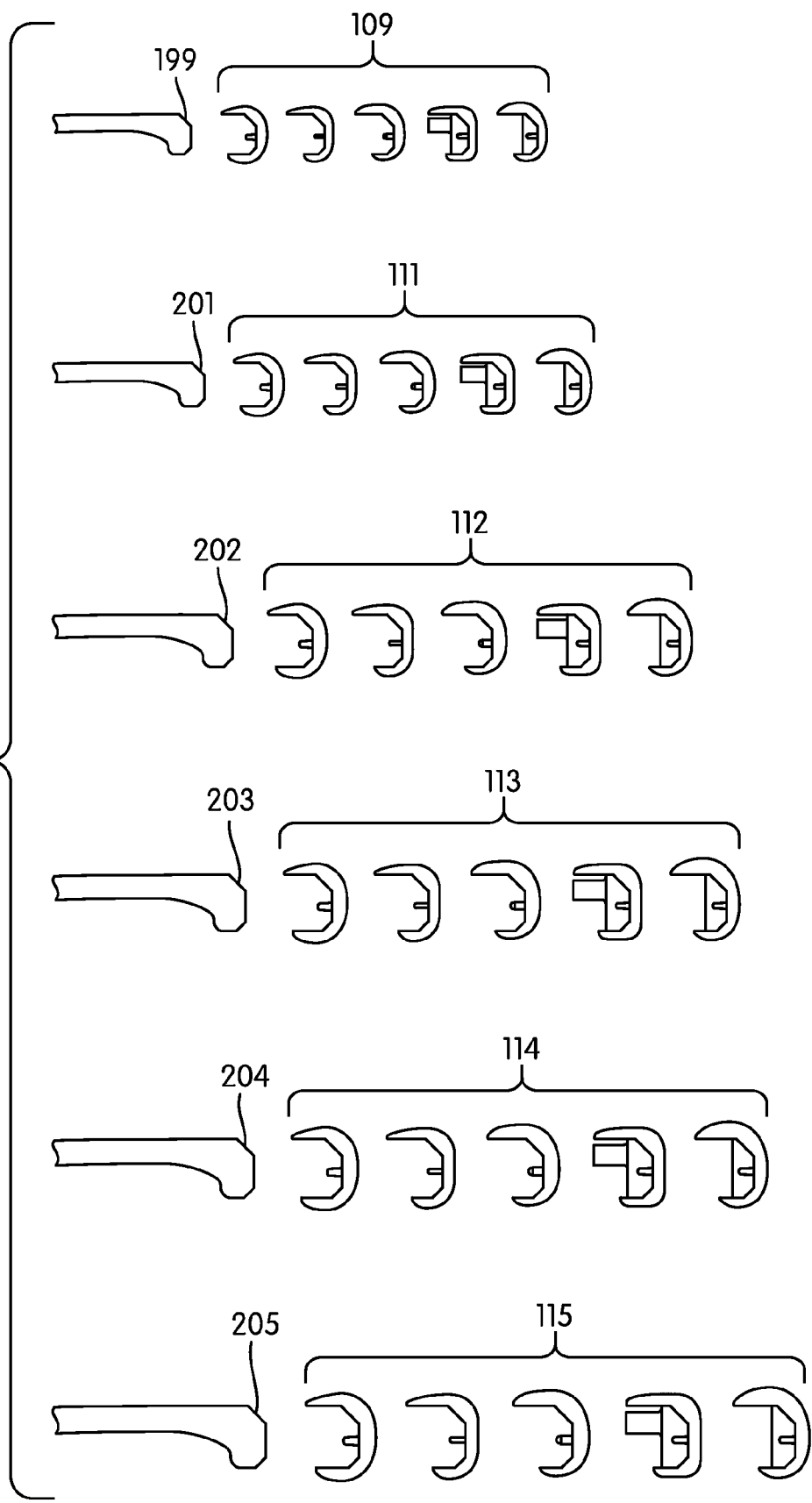
FIG. 5 is a side view of a preferred embodiment of the TKA system that encompasses six sizes of the 5 different TKA femoral prosthesis designs illustrated in FIG. 4.

In some embodiments, universal TKA systems may be provided in different sizes. Any desired number of sizes of universal TKA systems may be provided. One example of a series of universal TKA systems in different sizes is illustrated in FIG. 5, where six sizes of universal TKA systems are shown. Of course it is possible to provide more or less than six sizes of universal TKA systems. The embodiment shown in FIG. 5 is merely an example.

Referring to FIG. 5, first distal femur surface 199 corresponds to a first set of femoral components 109. Each of the femoral components of the first set of femoral components 109 preferably includes a substantially similar proximal surface that is configured to mate with first distal femur surface 199. First distal femur surface 199 may be prepared with a first universal cutting jig (not shown). For clarity, tibial components that correspond to each of the femoral components of the first set of femoral components 109 are not shown in FIG. 5, but may be provided with each of the femoral components. The first universal cutting jig along with the first set of femoral components 109 and their corresponding tibial components may be referred to as the first universal TKA system. As shown schematically in FIG. 5, the first universal TKA system can be provided in a first relatively small size.

Second distal femur surface 201 corresponds with a second set of femoral components 111. Each of the femoral components of the second set of femoral components 111 preferably includes a substantially similar proximal surface that is configured to mate with second distal femur surface 201. Second distal femur surface 201 may be prepared with a second universal cutting jig (not shown). For clarity, tibial components that correspond to each of the femoral components of the second set of femoral components 111 are not shown in FIG. 5, but may be provided with each of the femoral components. The second universal cutting jig along with the second set of femoral components 111 and their corresponding tibial components may be referred to as the second universal TKA system. As shown schematically in FIG. 5, the second universal TKA system may be larger than the first universal TKA system.

Third distal femur surface 202 corresponds with a third set of femoral components 112. Each of the femoral components of the third set of femoral components 112 preferably includes a substantially similar proximal surface that is configured to mate with third distal femur surface 202. Third distal femur surface 202 may be prepared with a third universal cutting jig (not shown). For clarity, tibial components that correspond to each of the femoral components of the third set of femoral components 112 are not shown in FIG. 5, but may be provided with each of the femoral components. The third universal cutting jig along with the third set of femoral components 112 and their corresponding tibial components may be referred to as the third universal TKA system. As shown schematically in FIG. 5, the third universal TKA system may be larger than the second universal TKA system.

Fourth distal femur surface 203 corresponds with a fourth set of femoral components 113. Each of the femoral components of the fourth set of femoral components 113 preferably includes a substantially similar proximal surface that is configured to mate with first distal femur surface 203. Fourth distal femur surface 203 may be prepared with a fourth universal cutting jig (not shown). For clarity, tibial components that correspond to each of the femoral components of the fourth set of femoral components 113 are not shown in FIG. 5, but may be provided with each of the femoral components. The fourth universal cutting jig along with the fourth set of femoral components 113 and their corresponding tibial components may be referred to as the fourth universal TKA system. As shown schematically in FIG. 5, the fourth universal TKA system may be larger than the third universal TKA system.

Fifth distal femur surface 204 corresponds with a fifth set of femoral components 114. Each of the femoral components of the fifth set of femoral components 114 preferably includes a substantially similar proximal surface that is configured to mate with fifth distal femur surface 204. Fifth distal femur surface 204 may be prepared with a fifth universal cutting jig (not shown). For clarity, tibial components that correspond to each of the femoral components of the fifth set of femoral components 114 are not shown in FIG. 5, but may be provided with each of the femoral components. The fifth universal cutting jig along with the fifth set of femoral components 114 and their corresponding tibial components may be referred to as the fifth universal TKA system. As shown schematically in FIG. 5, the fifth universal TKA system may be larger than the fourth universal TKA system.

Sixth distal femur surface 205 corresponds with a sixth set of femoral components 115. Each of the femoral components of the sixth set of femoral components 115 preferably includes a substantially similar proximal surface that is configured to mate with sixth distal femur surface 205. Sixth distal femur surface 205 may be prepared with a sixth universal cutting jig (not shown). For clarity, tibial components that correspond to each of the femoral components of the sixth set of femoral components 115 are not shown in FIG. 5, but may be provided with each of the femoral components. The sixth universal cutting jig along with the sixth set of femoral components 115 and their corresponding tibial components may be referred to as the sixth universal TKA system. As shown schematically in FIG. 5, the sixth universal TKA system may be larger than the firth universal TKA system.

Additional universal TKA systems of different sizes may also be provided. For example, embodiments may include seventh, eighth and ninth universal TKA systems that are larger than the sixth universal TKA system. Any desired number of universal TKA systems in any number of sizes may be provided.

Because the proximal surfaces of each set of femoral components are substantially similar for a given size, the universal TKA system provides multitude TKA femoral prosthesis designs for a given size femur along with a multitude of sizes to accommodate the variation in anatomy patient to patient. This universal TKA system can provide significant logistical benefits to hospitals and surgical centers because only a single universal cutting jig needs to be stocked for each size. The universal cutting jig for a particular size can be used to prepare the distal femur, and any desired compatible TKA system can then be implanted. Without this universal TKA system, hospitals and surgical centers need to stock a particular cutting jig with each different TKA system. This can add significant complexity and cost to the storage and management of TKA systems.

Figure 6:
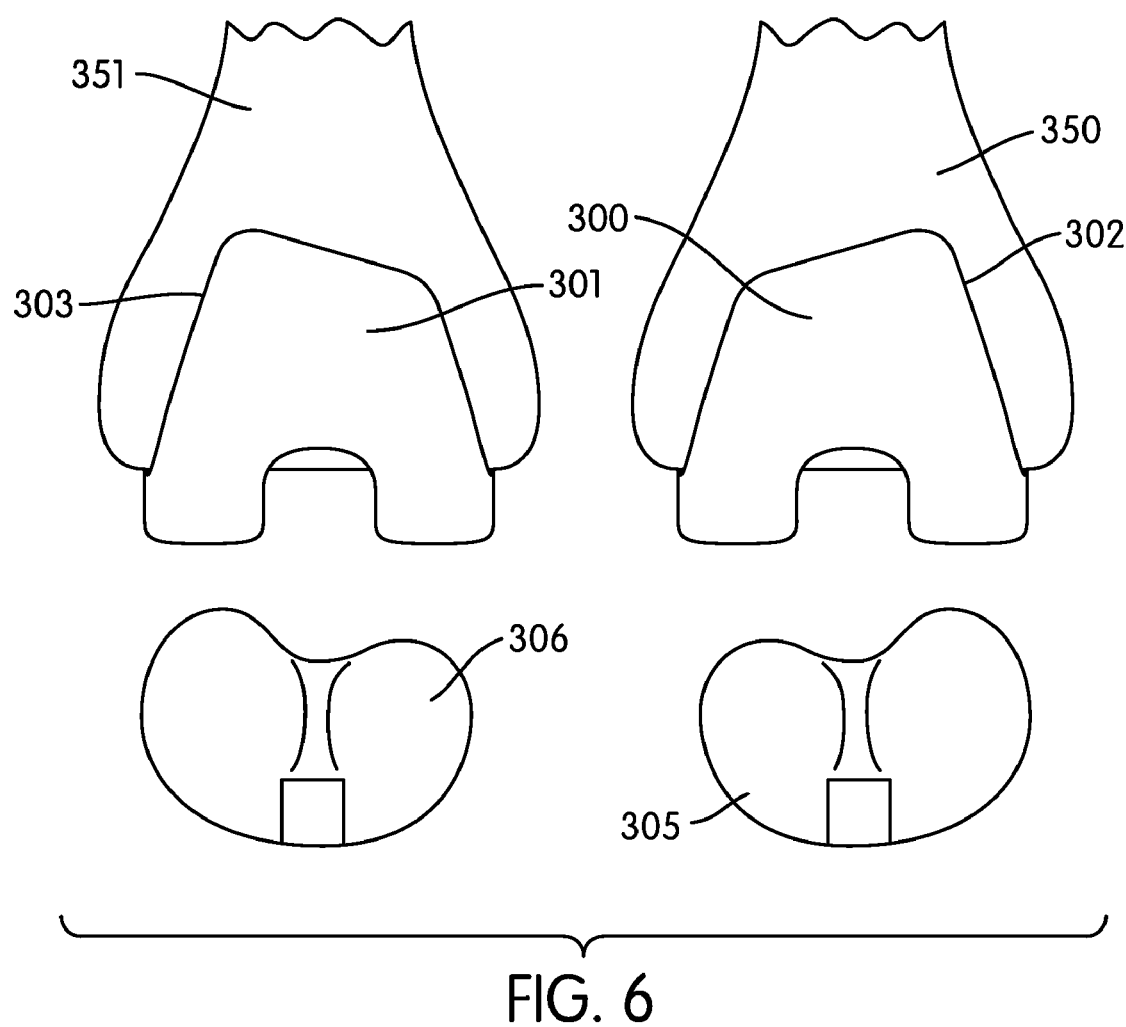
FIG. 6 is a top down view of a preferred embodiment of a left and right femoral prosthesis.

Typically, femoral prosthesis designs are configured for either a left or right femur and tibia. FIG. 6 illustrates an embodiment of a femoral prosthesis design where left femoral component 300 is attached to left femur 350 and associated with left tibia 305. In particular, femoral component 300 is larger along first medial side 302, to accommodate the general shape of left femur 350. Likewise, right femoral component 301 is attached to right femur 351 and associated with right tibia 306. In this case, right femoral component 301 is larger along second medial side 303, to accommodate the general shape of right femur 351.

Preferably, a universal TKA system includes provisions for associating a femoral component with either a left or right femur and the associated left and right tibia. To achieve this, universal femoral component 310, seen in FIGS. 7 and 8, may be configured to be the average of right femoral component 301 and left femoral component 300. In other words, universal femoral component 310 is not configured to fit either a left femur or a right femur exactly, but universal femoral component 310 may instead be configured to approximately fit both a left femur and a right femur. In a preferred embodiment, an average shape is used, however, in other embodiments, any desired shape that can be used for both left and right configurations may be used.

Figure 7:
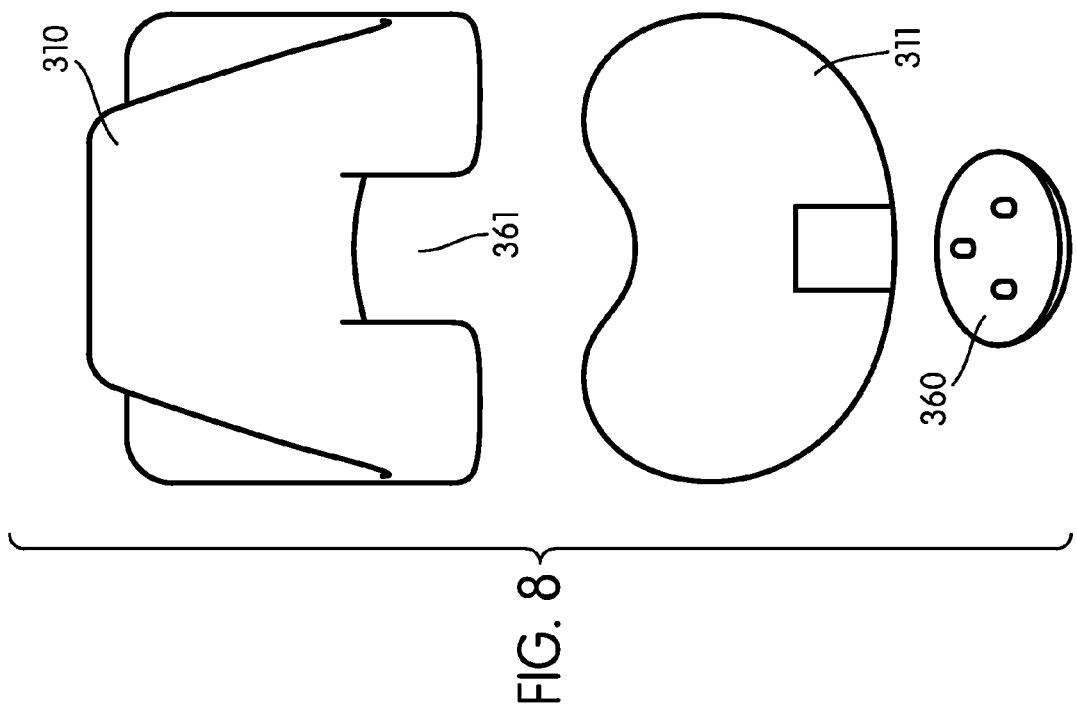
FIG. 7 is a top down view of a preferred embodiment of a left and right femoral prosthesis averaged together.
Figure 8:
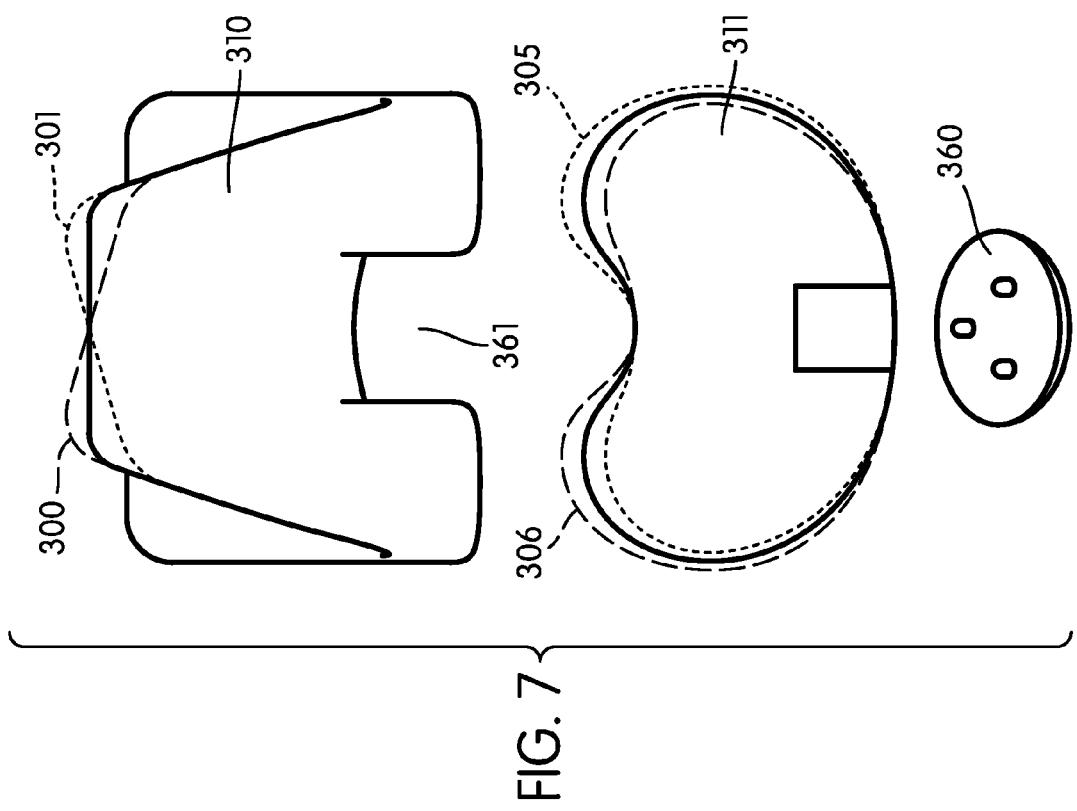
FIG. 8 is a top down view of a preferred embodiment of a universal femoral prosthesis.

Additionally, universal femoral component 310 may be configured to mate with tibia 311, which is seen from FIGS. 7 and 8 to be an average of right tibia 306 and left tibia 305. In other words, universal femoral component 310 may not be configured to fit left tibia 305 or right tibia 306 exactly, but universal femoral component may instead be configured to fit universal tibial component 311.

Universal patella component 360 can be symmetric or asymmetric in shape and be configured to mate with the femoral patella grove 361. As is known in the art, patella component 360 is preferably mounted to the prepared under surface of patella 902 (see FIG. 9). Possible patella components that may be used are disclosed in Scott et al. (U.S. Pat. No. 5,593,450) and Imbert (U.S. Pat. No. 4,344,192), the entirety of both patents are hereby incorporated by reference.

Using this preferred configuration, the femoral prosthesis design discussed throughout this detailed description may be used universally with either a left or right knee. This universal left/right configuration may further reduce the number of components that must be stored in a hospital, for various TKA systems. Instead of having to store a set of left femoral components and right femoral components, the hospital or surgical center may only need to store a single set of universal femoral components, effectively reducing the number or stored components in half.

It should be understood that the current femoral prosthesis design may also be used universally with either a left or right high flexion knee prosthesis. The term, "high flexion knee," as used throughout this specification and claims means a knee that can bend 120 degrees or more. Generally, a high flexion knee prosthesis is able to undergo about a 150 degree flexion angle, similar to the high flexion angle achieved by a human knee. This is in contrast to previous prostheses where the maximum flexion angle has been restricted to smaller angles, such as 109 degrees. A high flexion knee system may be especially important in Asian and African countries, where squatting and kneeling may be an integral part of daily life.

Figure 9:
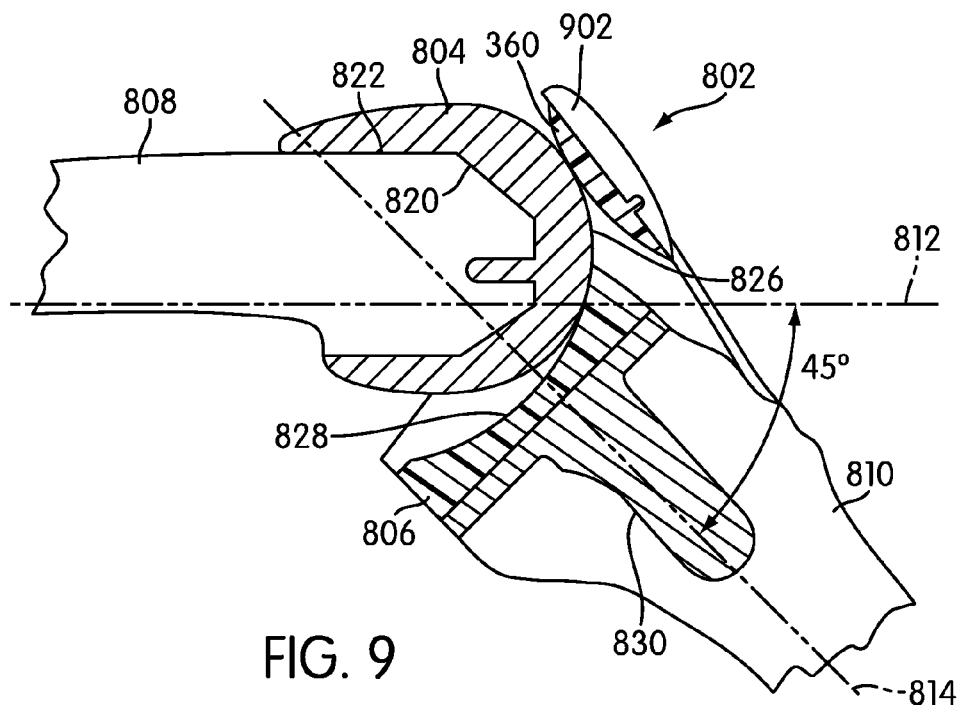
FIG. 9 is a side view of a preferred embodiment of a universal replacement knee undergoing bending.
Figure 10:
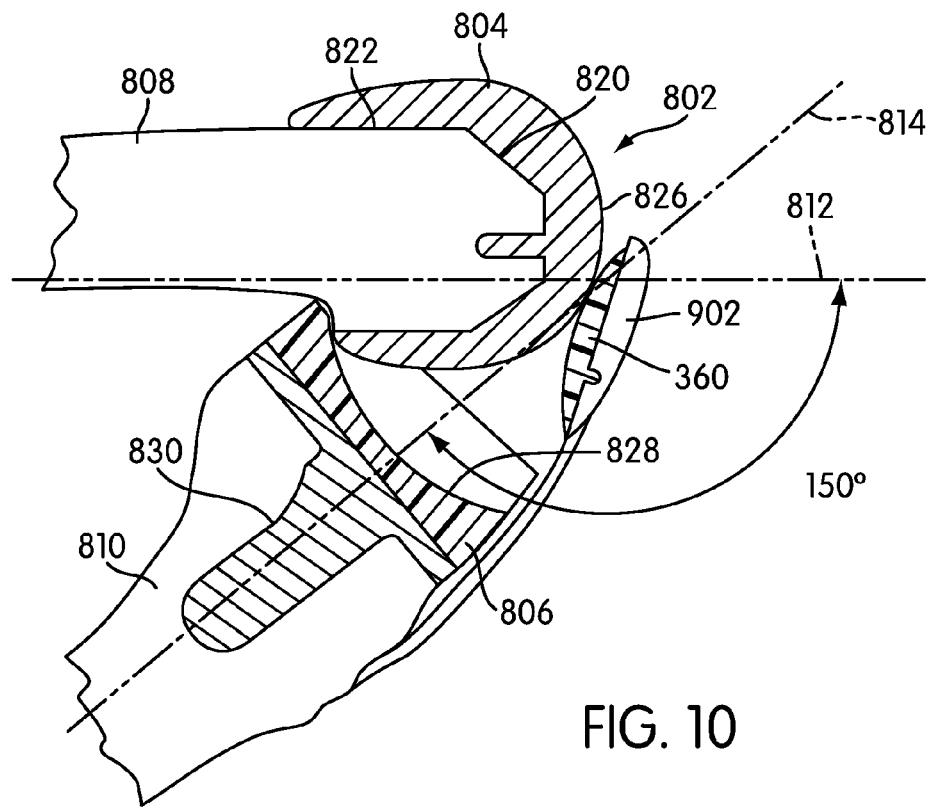
FIG. 10 is a side view of a preferred embodiment of a universal replacement knee achieving a high flexion angle.

FIGS. 9 and 10 are schematic side cross sectional views of universal replacement knee 802 that has been attached using a universal TKA system, undergoing bending. In this preferred embodiment, universal replacement knee 802 comprises femoral component 804 and tibial component 806, attached to femur 808 and tibia 810, respectively, and patella component 360 attached to patella 902.

In this embodiment, femoral component 804 includes proximal side 820 configured to fit with prepared distal surface 822 of femur 808. Preferably, prepared distal surface 822 has been formed using a universal cutting jig, as discussed previously. Femoral component 804 further includes distal side 826, configured to contact inner surface 828 of tibial component 806. As seen in the figures, tibial component 806 has been implanted into tibia 810, and in particular, protrusion 830 has penetrated into tibia 810.

Preferably, femoral component 804 and tibial component 806 may move in a way that allows femur 808 and tibia 810 to bend. As previously discussed, distal side 826 may slide within inner surface 828, allowing for this movement. In FIG. 9, replacement knee 802 has a flexion angle of 45 degrees. In other words, first central axis 814, associated with tibia 810, is disposed at an angle of 45 degrees from second central axis 812 that is associated with femur 808. This amount of bending represents a light degree of bending that may occur during walking or similar activities.

In FIG. 10, replacement knee 802 has a flexion angle of about 150 degrees, similar to the maximum flexion angle achieved with the human knee. This high flexion angle may be associated with activities such as squatting or kneeling. Thus, using the universal TKA system discussed throughout this detailed description, a user may experience the full range of motion in the knee. This is in contrast to previous TKA systems, where a prosthesis may achieve a high flexion angle but may not be used with both the left and right sides.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A system for performing a total knee replacement surgery comprising:
   a cutting member;
   a single jig configured to guide the cutting member in cutting a distal portion of a femur to form a prepared distal surface, the prepared distal surface having a prepared shape;
   a first femoral component having a first proximal side;
   a second femoral component having a second proximal side;
   the first proximal side and the second proximal side being substantially similar and configured to engage the prepared shape;
   the first femoral component having a first distal side;
   the second femoral component having a second distal side;
   wherein the first distal side is shaped differently than the second distal side;
   a first tibial component having a first inner surface shaped to receive the first distal side of the first femoral component but not the second distal side of the second femoral component:
   a second tibial component having a second inner surface shaped to receive the second distal side of the second femoral component but not the first distal side of the first femoral component;
   wherein the first femoral component and the second femoral component are configured to be used with either a left femur or a right femur;
   wherein the first tibial component and the second tibial component are configured to be used with either a left tibia or a right tibia;
   wherein the first femoral component and the first tibial component are configured to engage each other in a first high flexion knee prosthesis able to achieve a flexion angle of greater than 120 degrees; and
   wherein the second femoral component and the second tibial component are configured to engage each other in a second high flexion knee prosthesis able to achieve a flexion angle of greater than 120 degrees.

2. The system according to claim 1, wherein the first femoral component comprises approximately an average of a left femoral component and a right femoral component and the first tibial component comprises approximately an average of a left tibial component and a right tibial component.

3. The system according to claim 1, wherein the first femoral component, the second femoral component, the first tibial component, and the second tibial component are symmetrical.

4. The system according to claim 1, wherein a third femoral component includes a third proximal side being substantially similar to the first proximal side and wherein the third femoral component includes a third distal side that is shaped differently than either the first distal side or the second distal side.

5. The system according to claim 1, wherein the jig is different from a second jig, the second jig is configured to guide the cutting member in cutting a second distal portion of a femur and resulting in a second prepared distal surface, the second prepared distal surface having a second prepared shape; wherein the second prepared shape is different from the prepared shape.

6. A kit of parts comprising:
   a plurality of sets of knee prostheses, each including a femoral component and a tibial component; and
   a single cutting jig configured to guide a cutting member in cutting a distal portion of a femur to form a prepared distal surface on the femur, the prepared distal surface having a prepared shape;
   each femoral component of the plurality of sets of knee prostheses including a proximal side and a distal side;
   wherein the proximal side of each femoral component is substantially similar in size and shape corresponding with the prepared shape;
   wherein the distal side of each femoral component is shaped differently;
   wherein each femoral component has a corresponding tibial component to match the distal side of the femoral component;
   wherein each femoral component is configured to be used with either a left femur or a right femur;
   wherein each tibial component is configured to be used with either a left tibia or a right tibia; and
   wherein each femoral component and its matched tibial component are configured to engage each other in a high flexion knee prosthesis able to achieve a flexion angle of greater than 120 degrees.

7. The kit of parts according to claim 6, wherein each set of the plurality of sets of knee prostheses is configured to fit a particular size of femur.

8. The kit of parts according to claim 6, wherein each femoral component comprises approximately an average of a left femoral component and a right femoral component and each tibial component comprises approximately an average of a left tibial component and a right tibial component.

9. The kit of parts according to claim 6, wherein each set of the plurality of sets of knee prostheses further includes a symmetrical patella component configured to mate with the femoral component.

10. The kit of parts according to claim 6, wherein each femoral component and its matched tibial component are configured to engage each other in a high flexion knee prosthesis able to achieve a flexion angle of about 150 degrees.

11. The kit of parts according to claim 6, wherein the jig is used to shape the distal end of a femur for attaching a femoral component.

12. A system for performing a total knee replacement surgery on a left or right knee comprising:
   a single jig configured to guide a cutting member in cutting a distal portion of a left femur to expose cut surfaces on the left femur including at least first and second cut surfaces and resulting in a prepared left distal surface including the first and second left femur cut surfaces, the prepared left distal surface having a first prepared shape, the jig including a plurality of slots extending through the jig to guide the cutting member, the plurality of slots including a first slot to guide the cutting member to form the first left femur cut surface and a second slot to guide the cutting member to form the second left femur cut surface, the second slot oriented diagonally to the first slot and having a pair of opposing guide surfaces;
   the jig configured to guide the cutting member in cutting a distal portion of a right femur to expose cut surfaces on the right femur including at least first and second cut surfaces and resulting in a prepared right distal surface including the first and second right femur cut surfaces, the prepared right distal surface having a second prepared shape;
   wherein the first prepared shape and the second prepared shape are substantially identical and configured to receive a universal femoral component for use in either a right knee or a left knee, a set of at least two universal femoral components, each femoral component having a proximal side corresponding to the first prepared shape and the second prepared shape and a distal side that is different from distal sides of the remaining femoral components of the set;

a set of at least two tibial components, each tibial component matching a distinct femoral component of the set of at least two universal femoral components, wherein each femoral component and each tibial component is configured to be used with either a right knee or a left knee; and wherein each femoral component and its matching tibial component are configured to engage each other in a high flexion knee prosthesis able to achieve a flexion angle of greater than 120 degrees.

13. The system according to claim 12, wherein each femoral component is approximately an average of a left femoral component and a right femoral component.

14. The system according to claim 12, further comprising a symmetrical patella component configured to mate with any femoral component of the set of at least two universal femoral components.

15. The system according to claim 12, wherein each femoral component and each tibial component is symmetrical.

16. The system according to claim 12, wherein each tibial component comprises approximately an average of a left tibial component and a right tibial component.

17. The system according to claim 12, wherein each femoral component and its matching tibial component are configured to engage each other in a high flexion knee prosthesis able to achieve a flexion angle of about 150 degrees.

18. The system according to claim 12, wherein the sizes of the universal femoral components are similar.

19. A system for performing a total knee replacement surgery comprising:
  a single jig configured to guide a cutting member in cutting a distal portion of a femur and resulting in a prepared distal surface, the prepared distal surface having a prepared shape;
  a first femoral component having a first proximal side;
  a second femoral component having a second proximal side;
  the first proximal side and the second proximal side being substantially similar and configured to engage the prepared shape;
  the first femoral component having a first distal side that is different from a second distal side of the second femoral component;
  a first tibial component having a first inner surface shaped to receive the first distal side of the first femoral component but not the second distal side of the second femoral component;
  a second tibial component having a second inner surface shaped to receive the second distal side of the second femoral component but not the first distal side of the first femoral component;
  wherein the first femoral component and the second femoral component are configured to be used with either a left femur or a right femur;
  wherein the first tibial component and the second tibial component are configured to be used with either a left tibia or a right tibia;
  wherein the first femoral component and the first tibial component are configured to engage each other in a first high flexion knee prosthesis able to achieve a flexion angle of greater than 120 degrees; and
  wherein the second femoral component and the second tibial component are configured to engage each other in a second high flexion knee prosthesis able to achieve a flexion angle of greater than 120 degrees.

20. The system according to claim 19, further comprising a symmetrical patella component configured to mate with either of the first femoral component and the second femoral component.

21. The system according to claim 19, wherein the first high flexion knee prosthesis and the second high flexion knee prosthesis are able to achieve a flexion angle of about 150 degrees.

22. The system according to claim 19, wherein the first femoral component, the second femoral component, the first tibial component, and the second tibial component are sized for a first sized femur, and wherein the system further comprises:
  a second jig configured to guide a cutting member in cutting a distal portion of a femur and resulting in a second prepared distal surface, the second prepared distal surface having a second prepared shape;
  a third femoral component having a third proximal side;
  a fourth femoral component having a fourth proximal side;
  the third proximal side and the fourth proximal side being substantially similar and configured to engage the second prepared shape;
  the third femoral component having a third distal side that is different from a fourth distal side of the fourth femoral component;
  a third tibial component having a third inner surface shaped to receive the third distal side of the third femoral component but not the fourth distal side of the fourth femoral component;
  a fourth tibial component having a fourth inner surface shaped to receive the fourth distal side of the fourth femoral component but not the third distal side of the third femoral component;
  wherein the third femoral component and the fourth femoral component are configured to be used with either a left femur or a right femur;
  wherein the third tibial component and the fourth tibial component are configured to be used with either a left tibia or a right tibia;
  wherein the third femoral component and the third tibial component are configured to engage each other in a third high flexion knee prosthesis able to achieve a flexion angle of greater than 120 degrees;
  where the fourth femoral component and the fourth tibial component are configured to engage each other in a fourth high flexion knee prosthesis able to achieve a flexion angle of greater than 120 degrees;
  wherein the third femoral component, the fourth femoral component, the third tibial component, and the fourth tibial component are sized for a second sized femur; and
  wherein the first sized femur and the second sized femur are different sizes.

23. The system according to claim 19, wherein the first femoral component comprises approximately an average of a left femoral component and a right femoral component and the first tibial component comprises approximately an average of a left tibial component and a right tibial component.

24. The system according to claim 19, wherein the first femoral component, the second femoral component, the first tibial component, and the second tibial component are symmetrical.

25. The system according to claim 19, further comprising a plurality of additional femoral components,
  wherein each of the additional femoral components:
    has a proximal side that is substantially similar to the first proximal side and the second proximal side and is configured to engage the prepared shape,
    has a distal side that is different from distal sides of the remaining femoral components,
    is configured to be used with either a left femur or a right femur, and
    is configured to engage a corresponding tibial component in a high flexion knee prosthesis able to achieve a flexion angle of greater than 120 degrees.

26. The system according to claim 1, wherein the jig is configured to guide the cutting member in cutting a distal portion of a femur to form a plurality of cut surfaces on the femur including a first surface and a second surface oriented diagonally to the first surface and resulting in the prepared distal surface including the first and second surfaces, the jig including:
  a first region;
  an opposite second region to secure the jig to the distal portion of the Femur;
  a first slot extending through the jig from the first region to the second region to guide the cutting member while cutting the first cut; and
  a second slot extending through the jig from the first region to the second region and having a pair of opposing guide walls to guide the cutting member while cutting the second cut, the second slot oriented diagonally to the first slot; and
  wherein the jig further includes a third slot extending through the jig from the first region to the second region to guide the cutting member while cutting the distal portion of the femur to form a third surface oriented similar to the first surface, the third slot oriented similar to the first slot.

27. The system according to claim 26, wherein the jig further includes a fourth slot extending through the jig from the first region to the second region to guide the cutting member while cutting the distal portion of the femur to form a fourth surface disposed diagonally to the third surface, the fourth slot oriented diagonally to the third slot.

28. The system according to claim 27, wherein the jig further includes a recess formed at the first region to provide an entry for the cutting member to the second and fourth diagonally oriented slots.

* * * * *